United States Patent
Simske et al.

(10) Patent No.: US 7,310,648 B2
(45) Date of Patent: Dec. 18, 2007

(54) SYSTEM FOR COMPRESSION OF PHYSIOLOGICAL SIGNALS

(75) Inventors: Steven J. Simske, Fort Collins, CO (US); Daniel R. Blakley, Philomath, OR (US); Tong Zhang, San Jose, CA (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 464 days.

(21) Appl. No.: 10/942,228

(22) Filed: Sep. 15, 2004

(65) Prior Publication Data

US 2006/0059324 A1 Mar. 16, 2006

(51) Int. Cl.
*G06F 15/42* (2006.01)
*H03M 7/30* (2006.01)
*G11C 29/40* (2006.01)

(52) U.S. Cl. ........................ 707/101; 711/172
(58) Field of Classification Search ............ None
See application file for complete search history.

(56) References Cited

U.S. PATENT DOCUMENTS

| | | | |
|---|---|---|---|
| 4,754,483 A | 6/1988 | Weaver | |
| 4,947,858 A | 8/1990 | Smith | |
| 5,238,001 A * | 8/1993 | Gallant et al. | 600/513 |
| 5,506,872 A * | 4/1996 | Mohler | 375/240 |
| 5,623,935 A | 4/1997 | Faisandier | |
| 5,657,398 A | 8/1997 | Guilak | |
| 5,709,216 A | 1/1998 | Woodson, III | |
| 5,832,490 A | 11/1998 | Riley | |
| 5,836,889 A | 11/1998 | Wyborny et al. | |
| 5,944,745 A * | 8/1999 | Rueter | 607/27 |
| 6,049,765 A * | 4/2000 | Iyengar et al. | 704/201 |
| 6,152,883 A | 11/2000 | Blanchett et al. | |
| 6,200,265 B1 | 3/2001 | Walsh | |
| 6,599,242 B1 | 7/2003 | Splett et al. | |
| 6,795,218 B1 | 9/2004 | Falzon | |
| 6,976,026 B1 * | 12/2005 | Getzinger et al. | 707/101 |
| 2002/0082867 A1 | 6/2002 | MacCarter | |
| 2002/0118306 A1 * | 8/2002 | Lee | 348/714 |
| 2002/0198445 A1 | 12/2002 | Dominguez | |
| 2004/0215270 A1 * | 10/2004 | Ritscher et al. | 607/27 |

FOREIGN PATENT DOCUMENTS

| | | |
|---|---|---|
| EP | 0 472 441 A1 | 2/1992 |
| EP | 1 037 470 A1 | 9/2000 |

OTHER PUBLICATIONS

Jalaleddine, Sateh M.S., Chriswell G. Hutchens, Robert D. Strattan, and William A. Coberly, "ECG Data Compression Techniques—A Unified Approach," IEEE Transactions on Biomedical Engineering, vol. 37, No. 4, Apr. 1990, pp. 329-343.

(Continued)

*Primary Examiner*—B. James Peikari (57) ABSTRACT

A method of optimizing retention of signal information from a physiologically generated digital signal is provided. The method can comprise steps of generating a digital signal from a physiological source, storing the digital signal into a memory location as a stored digital signal, identifying within the stored digital signal a preferred digital signal event exclusive of a non-preferred digital signal event, wherein the preferred digital signal event has a first event compression level and the non-preferred digital signal event has a second event compression level, detecting a memory storage limitation in the memory location, and increasing the second event compression level of the non-preferred digital signal event as a result of detecting a memory storage limitation. Also, the portable monitor can detect the presence of an upload source to which the digital signal can be uploaded in order to minimize the need to compress the signal.

33 Claims, 3 Drawing Sheets

OTHER PUBLICATIONS

Szilagyi, S.M., and L. Szilagyi, "Efficient ECG Signal Compression Using Adaptive Heart Model," 2001 Proceedings of the 23rd Annual EMBS International Conference, Oct. 25-28, Istanbul, Turkey, pp. 2125-2128.

Hamilton, Patrick S. and Willis J. Tompkins, "Compression of the Ambulatory ECG by Average Beat Subtraction and Residual Differencing," IEEE Transactions on Biomedical Engineering, vol. 38, No. 3, Mar. 1991, pp. 253-259.

Zigel, Yaniv, Arnon Cohen and Amos Katz, "ECG Signal Compression Using Analysis by Synthesis Coding," IEEE Transactions on Biomedical Engineering, vol. 47, No. 10, Oct. 2000, pp. 1308-1316.

Zigel, Yaniv, Arnon Cohen and Amos Katz, "The Weighted Diagnostic Distortion (WDD) Measure for ECG Signal Compression," IEEE Transactions on Biomedical Engineering, vol. 47, No. 11, Nov. 2000, pp. 1422-1430.

ASK; "ECG Electrodes, A Study of Electrical and Mechanical Long-term Properties"; Depts of Biomedical Eng & Dermatology, Sweden, Acta anaesth.scand. 1979, 23, pp. 189-206.

* cited by examiner

SYSTEM FOR COMPRESSION OF PHYSIOLOGICAL SIGNALS

FIELD OF THE INVENTION

The present invention relates generally to the compression of physiological signal data. More particularly, the present invention relates to the staggered compression of cardiac cycle data when physical memory storage may become a limiting factor.

BACKGROUND OF THE INVENTION

Many medical treatment regimens require the monitoring of specific physiological signals. For example, the treatment of various heart problems often depends on the collection and subsequent analysis of electrocardiogram (ECG) signals from a patient. Many abnormal heart rhythms that would be diagnostic in the treatment process, however, may occur with intermittent frequency and with little predictability. These abnormal heart rhythms may thus be unavailable to a medical practitioner when the patient's heart rhythms are monitored for only limited periods of time. In order to allow the collection of these intermittent, abnormal rhythms, or to monitor long stretches of heart activity over time, a portable heart monitor may be utilized. Portable heart monitors allow patients to escape the confines of a hospital bed and to be able to go about normal life while still allowing the collection of heart rhythms for diagnostic purposes.

Heart rhythms are generally digitally sampled by an analogue to digital converter and stored in physical memory. Each point of the sampled signal is typically represented by two numeric values, one for amplitude and the other for time. A higher sampling rate requires more physical memory storage to store the signal. While decreasing the sampling rate will decrease the size of the recorded signal, unacceptable degradation to the reconstituted signal can occur from a diagnostic point of view. For example, some cardiac waveforms contain energy above 60 Hz, and thus a sampling rate below 60 Hz will result in the loss of that signal information.

While physical memory limitations tend to be insignificant in hospital and clinical locations, portable heart monitors have limited memory storage. These memory limitations are even more severe in implantable heart monitors where memory storage space, power limitations, processing time, and cost are prime considerations.

Traditional data compression techniques may alleviate this problem to some extent but prove to be inflexible to the often dynamic needs of the medical practitioner and the patient. For example, if the cardiac signal is highly compressed to allow for a maximum recording time, but the patient wears the heart monitor for a much shorter length of time, signal information can be needlessly lost that may be vital to the diagnostic process. Conversely, if the cardiac signal is lightly compressed to allow for the recording of maximum signal information, and the patient wears the heart monitor for a longer period of time than the memory storage allows, signal data can be lost that may be vital to the diagnostic process.

SUMMARY OF THE INVENTION

It has been recognized that it would be advantageous to provide a portable monitor that adapts to maximize the preservation of signal information in a physiological signal as the duration of usage of the device changes. It would also be beneficial for the portable monitor to function under different compression schemes depending on the amount of available storage. Specifically, a method of optimizing retention of signal information from a physiologically generated digital signal is provided. The method can comprise steps of generating a digital signal from a physiological source, storing the digital signal into a memory location as a stored digital signal wherein the stored digital signal has a stored compression level, and detecting a memory storage limitation in the memory location. The method can also include a step of increasing the stored compression level of at least a portion of the stored digital signal in the memory location as a result of the memory storage limitation in the memory location.

Another method of optimizing retention of signal information from a physiologically generated digital signal is provided. The method can comprise steps of generating a digital signal from a physiological source and storing the digital signal into a memory location as a stored digital signal. Other steps can include identifying within the stored digital signal a preferred digital signal event exclusive of a non-preferred digital signal event wherein the preferred digital signal event has a first event compression level and the non-preferred digital signal event has a second event compression level, detecting a memory storage limitation in the memory location, and increasing the second event compression level of the non-preferred digital signal event as a result of detecting a memory storage limitation.

The present invention can also be embodied as a system for optimizing retention of signal information from a physiologically generated digital signal. The system can comprise a signal recorder having an online mode and a remote mode with an online detection unit to detect when the signal recorder is in the online mode. The system can also comprise an online memory module operationally coupled to the signal recorder when in the online mode, such that the digital signal is stored in the online memory module when the signal recorder is in the online mode. The system also includes a local memory module operationally coupled to the signal recorder when in the remote mode, such that the digital signal is stored in the local memory module as a stored digital signal when the signal recorder is in the remote mode. The system may also include a local memory monitor operationally coupled to the local memory module to detect a memory storage limitation in the local memory module, a compression unit operationally coupled to the local memory module to compress at least a portion of a stored digital signal recorded by the signal recorder, and a control unit operationally coupled to the local memory module to evaluate a compression level of the stored digital signal.

Additional features and advantages of the invention will be apparent from the detailed description which follows, taken in conjunction with the accompanying drawings, which together illustrate, by way of example, features of the invention.

DETAILED DESCRIPTION OF THE PREFERRED EMBODIMENTS

Reference will now be made to the exemplary embodiments illustrated in the drawings, and specific language will be used herein to describe the same. It will nevertheless be understood that no limitation of the scope of the invention is thereby intended. Alterations and further modifications of the inventive features illustrated herein, and additional applications of the principles of the inventions as illustrated herein, which would occur to one skilled in the relevant art and having possession of this disclosure, are to be considered within the scope of the invention.

In describing and claiming the present invention, the following terminology will be used.

The singular forms "a," "an," and "the" include plural referents unless the context clearly dictates otherwise. Thus, for example, reference to "a memory module" includes reference to one or more of such modules.

As used herein, "lossless compression" refers to any compression technique that results in essentially no signal loss. In other words, if a signal has been compressed using a lossless compression method, the original signal can be essentially recreated in its entirety. Any form of lossless compression known to one skilled in the art can be utilized in the present invention, including, but not limited to, run-length, statistical (pattern substitution, Huffman), differential and differential Huffman, predictive encoding, and combinations thereof.

As used herein, "lossy compression" refers to any compression technique that results in signal information loss. In other words, once a signal has been compressed using a lossy compression method, the original signal cannot be recreated in its entirety. Lossy compression types may include any form of lossy compression known to one skilled in the art including wavelet, fractal, transform, vector quantization encoding, and combinations thereof. Lossy compression methods generally require less processing power to implement than lossless compression methods.

As used herein, the term "compression level" refers to the relative level of compression of a digital signal. Decreasing the compression level will result in a less compressed digital signal and a larger memory footprint, while increasing the compression level will result in a more compressed digital signal and a smaller memory footprint.

As used herein, the term "acquisition compression level" refers to the relative level of compression (or lack of compression) applied to the digital signal prior to its storage in physical memory. This type of compression can occur simultaneously with the recording of the digital signal, and as such may also be referred to as "on-the-fly" compression. If there is no compression at recording, then the acquisition compression level is a level of no compression.

As used herein, the term "storage compression level" refers to the relative level of any compression method applied to the digital signal subsequent to its storage in physical memory. A "storage compression level" can range from no compression to maximum compression.

As used herein, the term "digital signal event" refers to any distinguishable feature of a physiologically generated digital signal. For example, a single ECG cycle can be considered a digital signal event. Similarly, a portion of an ECG cycle, such as the PR segment, can be considered a digital signal event.

As used herein, the term "physiologically generated digital signal" refers to a digital signal that is generated as a result of a physiological process occurring in a human or animal body. Examples may include, but are not limited to, ECGs, VCGs, EMGs, or EEGs.

The term "about" when referring to a numerical value or range is intended to encompass the values resulting from experimental error that can occur when taking measurements.

With these definitions in mind, it has been recognized that a portable monitor that adapts to maximize the preservation of signal information in a physiological signal as the duration of usage of the device changes would be an advancement in the art. It would also be beneficial for the monitor to function under different compression schemes depending on the amount of available storage.

Embodiments of the present invention provide methods for maximizing the preservation of digital signal information as the duration and usage needs of a recording device changes. In an example of a portable heart monitor, the present invention will allow variable usage durations to dictate the amount of signal information content saved by the device. If the device is used for only short periods away from a potential upload source, the resulting recorded digital signal will be relatively less compressed than a digital signal resulting from more extended recording durations. This can be accomplished by utilizing a staggered compression scheme, wherein the relative level of compression is increased as the physical memory of the device becomes limited due to signal storage. Similarly, battery life has the potential to impact the storage ability of a portable device due to the energy intensive nature of compression methods, and thus can be considered when determining compression schemes. Additionally, processing capacity and the amount of available power can be considerations in the encoding and decoding of certain compression schemes.

Figure 1:
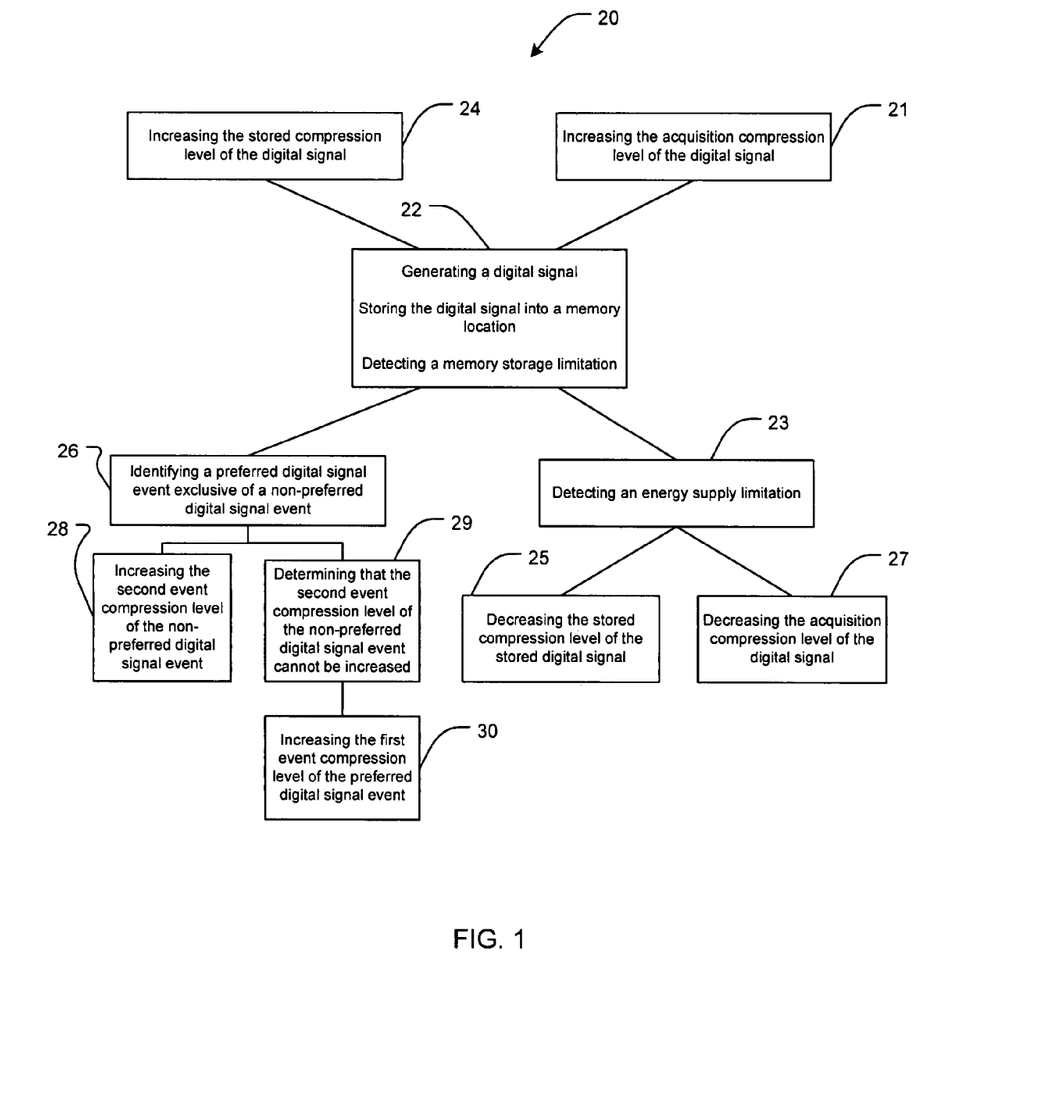
FIG. 1 is a graphical representation of a method of optimizing retention of signal information from a physiologically generated digital signal in accordance with an embodiment of the present invention.

FIG. 1 is a schematic representation of method steps from various embodiments of the present invention. As such, each graphically represented step is not necessarily used in every embodiment. Similarly, the order of the method steps as represented is not intended to be limiting, and as such, modification of step order is considered to be within the scope of the present invention.

As illustrated in FIG. 1, a method 20 of optimizing retention of signal information from a physiologically generated digital signal is disclosed. One aspect can comprise steps of generating from a physiological source a digital signal having an acquisition compression level, storing the digital signal into a memory location as a stored digital signal with a stored compression level, and detecting a memory storage limitation in the memory location 22. One embodiment further comprises a step of increasing the stored compression level of the digital signal 24 in the memory location as a result of the memory storage limitation in the memory location. Yet another embodiment includes steps of identifying a preferred digital signal event with a first event compression level exclusive of a non-preferred digital signal event 26 with a second event compression level, and increasing the second event compression level of the non-preferred digital signal event 28 in the memory location as a result of the memory storage limitation in the memory location. Initially, the first and second compression levels can be the same or different. Another embodiment further comprises a step of increasing the acquisition compression level of the digital signal 21 in response to detecting a memory storage limitation in the memory location. Still another possible embodiment includes a step of detecting an energy supply limitation 23 and decreasing the stored compression level of the stored digital signal 25 and/or decreasing the acquisition compression level of the digital signal 27. Still yet another embodiment includes steps of identifying a preferred digital signal event with a first event compression level exclusive of a non-preferred digital signal event 26 with a second event compression level, and determining that the second event compression level of the non-preferred digital signal event cannot be increased 29 and increasing the first event compression level of the preferred digital signal event 30 as a result of the memory storage limitation in the memory location.

The step of identifying a preferred digital signal event with a first event compression level exclusive of a non-preferred digital signal event 26 with a second event compression level can occur at any point prior to detecting a memory storage limitation. This would include identifying the preferred digital signal event prior to generating the digital signal or prior to storing the digital signal into a memory location. Also, this identification step can occur simultaneously with or after detecting a memory storage limitation.

Figure 2:
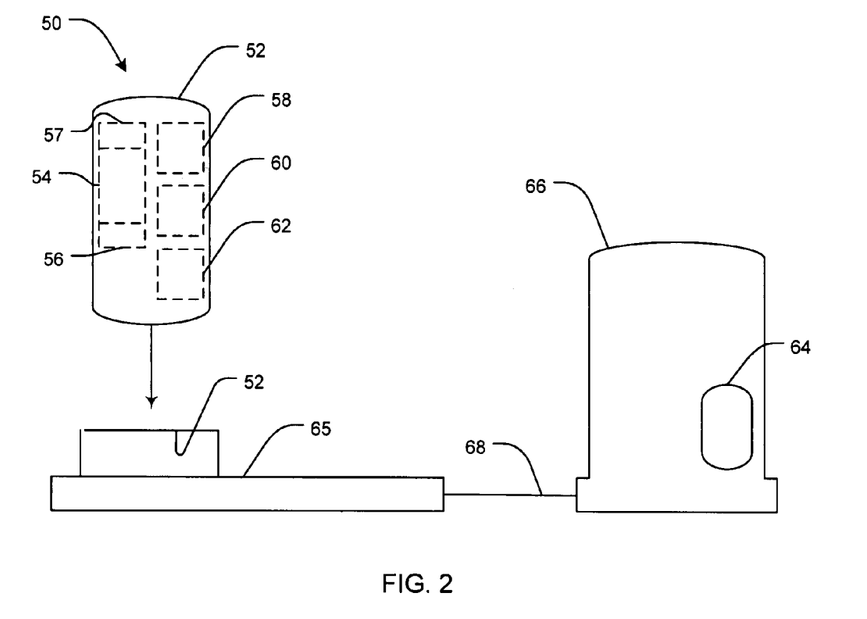
FIGS. 2-3 are schematic representations of systems for optimizing retention of signal information from physiologically generated digital signals in accordance with an embodiment of the present invention.

Turning to FIG. 2, the present invention can also be embodied as a system 50 for optimizing the retention of signal information from a physiologically generated digital signal. The system can comprise a signal recorder 52 having an online mode and a remote mode. The signal recorder can include a local memory module 54, a local memory monitor 56, a compression unit 58, a control unit 60, and an online detection unit 62, for example. Additionally, the system can include an acquisition compression unit 57 operationally coupled to the local memory module to compress the digital signal prior to the digital signal being stored as a stored digital signal in the local memory module. When in the online mode, as shown in FIG. 2, the system can further comprise an online memory module 64, located in a local server or computer 66, wherein the online memory module is operationally coupled to signal recorder via a docking station 65 and a communication pathway 68. The compression unit, the control unit, and the online detection unit can be hardware and/or software based, and can be embodied as functions of the same physical device. For example, a central processing unit can perform the functions of compression, control, and online detection. It should not be implied that a given unit is necessarily a single hardware or software device. Embodiments are contemplated in which a unit is purely functional in nature, and can be comprised of a number of hardware and/or software devices. It is understood that the hardware and/or software implementation of these units are well within the knowledge of one skilled in the art.

The compression unit 58 can be operationally coupled to the local memory module 54 to compress at least a portion of a stored digital signal recorded by the signal recorder 52. The compression of the digital signal can occur in the local memory module, in a cache buffer, or in any other manner known to one skilled in the art.

The control unit 60 can be operationally coupled to the local memory module 54 to evaluate the compression level of the stored digital signal. The control unit can also make determinations as to which portions of the digital signal to compress when the signal is differentially compressed, and which portions of the digital signal to dump from the local memory module when maximum compression has occurred and more memory storage space is required.

The online detection unit 62 can be operationally coupled to the control unit 60 to detect when the signal recorder 52 is in the online mode. When the online detection unit detects that the signal recorder is in the online mode, the digital signal can be uploaded to the online memory module 64, and thus further compression of the digital signal is not required. Even so, further compression of the digital signal prior to uploading or after storage in the online memory module is not precluded, and is considered to be within the scope of the present invention.

The online memory module 64 can be any device used for storing a digital signal known to one skilled in the art, including, without limitation, hard disk storage, a RAID array, RAM memory, optical disk storage, and combinations thereof.

The communication pathway 68 can be any type of data transmission means known to one skilled in the art, and it can be a physical or a wireless connection. For example, FIG. 2 shows an embodiment whereby the signal recorder 52 is coupled to a docking station 65. The docking station can then be coupled to online memory module 64 via the communication pathway. The online memory module can be associated with a local server or computer 66, a hospital mainframe, or any other data storage means known to one skilled in the art. As such, the communication pathway can be local wiring directly to the data storage means or network wiring within a hospital or clinic environment. Alternatively, the communication pathway can be any type of wireless communication means known to one skilled in the art.

The local memory module 54 can be operationally coupled to the signal recorder 52 when it is in the remote mode. A local memory monitor 56 can be operationally coupled to the local memory module to detect a memory storage limitation. The local memory monitor may be hardware or software based, depending on the configuration of the signal recorder. When the local memory monitor detects a memory supply limitation, the stored digital signal can be compressed to conserve space in the local memory module.

Figure 3:
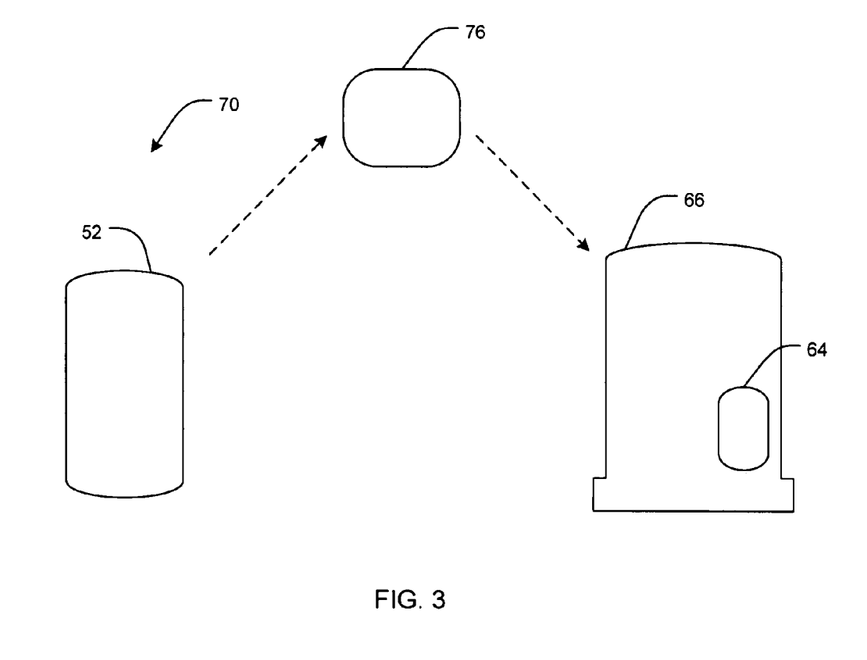

As shown in FIG. 3, the present invention can also be embodied as a system 70 for optimizing the retention of signal information from a physiologically generated digital signal. The digital signal can be transmitted from the signal recorder 52 to a cellular network 76, and then to the online memory module 64, located in local server or computer 66. This may be accomplished directly from the signal recorder or via a docking station coupled to a cellular transmitter. Direct transmission from the signal recorder is also contemplated, and would allow uploading of the digital signal to occur whenever the signal recorder was within range of the cellular network.

The signal recorder 52 and the online memory module 64 can function in a similar manner to that shown above in FIG. 2. Communication between the signal recorder and the online memory module, however, occurs via a cellular network 76. It is understood that the knowledge of a cellular network is well within the understanding of one skilled in the art.

The following is a general discussion of those aspects of the present invention that apply to multiple embodiments. It is assumed that not all embodiments strictly adhere to the following description, and variations are assumed to be within the scope of the present invention.

When the signal recorder is being used in the online mode, the signal recorder can upload a digital signal to the online memory module, thus reducing the need for signal compression due to greater memory storage capacity. The signal recorder can detect the online mode either through a wired or a wireless connection. Similarly, the uploading of the digital signal can be through a wired or wireless means. Upon uploading the digital signal, the local memory module can be cleared to free up space for additional digital signal recording.

When the signal recorder is being used in the remote mode, the signal recorder stores the digital signal to a local memory module. Because such local memory is often limited in terms of storage capacity, compression of the digital signal is required to minimize signal loss when the signal recorder is used for extended durations.

Upon detection of a memory storage limitation when in the remote mode, all or part of the stored digital signal can be compressed to free up space in the local memory module. Also, the acquisition compression level of the digital signal can be increased to allow compression prior to storage in the local memory module.

Such a memory storage limitation can be real or anticipated. A real memory storage limitation can occur when the local memory monitor detects that the local memory module has become essentially filled with digital signal data. An anticipated memory storage limitation can occur when the local memory monitor detects that the local memory module has become filled to a predetermined level. For example, the local memory monitor can detect that the local memory module is ⅔ full, or that memory space remains for only ½ hour of recording.

It is also contemplated that compression of the digital signal can be invoked according to certain use behaviors. In such a case, the signal recorder could detect a pattern of use and compress the digital signal accordingly. For example, a user may be offline and utilizing the signal recorder in the remote mode for 8 hours each day during a normal work week. The signal recorder can optimally compress the digital signal to conform to this predictable pattern of use, rather than in response to a memory limitation.

Also, situations may arise with the use of a portable monitor in the remote mode in which battery supply becomes limited. Because compression requires a greater expenditure of energy, battery life can be lengthened by reducing or eliminating compression altogether.

Data Compression

One skilled in the art will recognize that a wide variety of compression schemes can be effectively utilized in embodiments of the present invention. In one aspect, a step of increasing the stored compression level can result in a uniform increase of essentially all of the stored digital signal. In other words, the stored digital signal can be uniformly compressed without respect to the information content of any particular section of the stored digital signal.

Alternative aspects of the present invention can include method steps to allow a differential compression of sections of the stored digital signal based on specific information content. The method can include a step of identifying preferred digital signal events exclusive of non-preferred signal events. This identification can be a real-time classification or a "pre-classification" of segments of the digital signal. In the case of ECGs, for example, a preferred event may be all normal ECGs, all abnormal ECG's, or abnormal ECG's occurring in runs of at least five in number. The preferred digital signal event can have a first compression level and the non-preferred digital signal event can have a second event compression level. These two compression levels can be the same or different, depending on the circumstances. Similarly, a hierarchy of digital signal events can be established, each with a compression level specific to that digital signal event. This hierarchy represents the relative importance to a clinician of different categories of ECG information.

In order to preserve more preferred types of information given a limited memory supply, non-preferred digital signal events can be compressed to retain memory for storage of more preferred digital signal events. In one aspect, the second compression level of a non-preferred digital signal event can be increased without a concomitant increase in the first compression level of a preferred digital signal event. Similarly, both the second compression level and the first compression level can be increased simultaneously, but with the magnitude of the increase in the second compression level being greater. Another aspect of the method can include a step of determining that the second event compression level of the non-preferred digital signal event cannot be increased and increasing the first event compression level of the preferred digital signal event. The inability to compress the second event compression level may be due to a user selected criteria for maximum compressibility or due to the non-preferred digital signal event being already compressed to the maximum level available. In this way, the non-preferred digital signal events will be maximally compressed before the constraints of the limited memory supply require the compression of preferred digital signal events.

In another aspect of the present invention, the digital signal can initially be stored in the local memory location in an uncompressed state, or in other words, the acquisition compression level can be no compression, and thus, the digital signal can be stored as an uncompressed digital representation of the physiological signal. This uncompressed digital representation would contain the maximum amount of signal information available given the analogue-to-digital conversion rate of the recording device. In yet another aspect, however, the digital signal can have an acquisition compression level that is at least some compression, or in other words, the digital signal can be compressed prior to its storage into the local memory location. It is conceivable that this acquisition compression could take place concomitantly with the acquisition of the physiological signal, in a buffer location prior to storage into the local memory location, or at any other point subsequent to signal acquisition but prior to storage of the digital signal into the local memory location. In aspects utilizing acquisition compression where some compression occurs, the acquisition compression level of the digital signal can be increased in response to detecting a memory storage limitation in the memory location. The compression level can also be changed dynamically based on some combination of performance and available memory. For example, the compression level can be altered in response to a limitation of battery power and available memory. The compression level can also be altered in cases where the processor may be unable to keep pace with the current compression scheme in situations where noise related to physical motion is present in the digital signal, making it difficult to compute compression kernels, coefficients, etc. It is contemplated that any situation known to one skilled in the art that arises where functionality would be enhanced by altering the compression level is considered to be within the scope of the present invention.

Any form of data compression known to one skilled in the art may be utilized and is considered to be within the scope of the present invention. Specific types of signal compression are now described, and it should be understood that this description is not intended to be limiting in any way, but serves to give a broad view of the various compression types and levels thought to be useful in aspects of the present invention.

An example hierarchy of compression levels will now be described, beginning with the higher or more compressed levels. The compression levels are numbered for convenience, and these numbers are not intended to convey any other meaning. The descriptions will utilize exemplary ECG data as an example, but they are applicable to VCGs or any other appropriate physiological or other time-varying, periodic, predictable/modeled digital signal. Also, any number of compression levels can be utilized in any given aspect of the present invention. Similarly, different ranges of compression may be used, depending on the desired resolution range of the information content in the digital signal. Reference will be made to the beginning, peak, and end points of specific segments of the ECG cycle. It is well within the ability of one skilled in the art to determine these points within the PQRSTU wave.

In accordance with exemplary embodiments, sixteen different possible compression levels are provided below, which are referred to in descending order from 16 to 1.

Compression level 16 can indicate the number of total ECGs since the last time the digital signal was uploaded to the online memory location or module when the signal recorder was in the online mode.

Compression level 15 can indicate the number of normal ECGs and the number of abnormal ECGs since the last time the digital signal was uploaded to the online memory location or module when the signal recorder was in the online mode. Some ECG analysis will be performed to differentiate between a normal ECG and an abnormal ECG. Abnormality may be a generally defined ECG characteristic or may be predefined by a user to match one or more expected pathologies, such as ECGs characteristic of ventricular fibrillation, atrial fibrillation, etc.

Compression level 14 can include the data compression represented by compression level 15 plus histograms of ECG intervals. For example, an XML description of a normal ECG may be represented as follows:

```
<Normal ECG>
    <criteria>PR/RT ratio 0.67-1.5</criteria>
    <criteria>period 0.6-1.1 sec</criteria>
    <number>45,227</number>
    <0.6-0.7 sec>284</0.6-0.7 sec>
    <0.7-0.8 sec>11,344</0.7-0.8 sec>
    <0.8-0.9 sec>27,889</0.8-0.9 sec>
    <0.9-1.0 sec>4,725</0.9-1.0 sec>
    <1.0-1.1 sec>985</1.0-1.1 sec>
</Normal ECG>
```

In this example, PR/RT represents the ratio range of the PR interval to the RT interval required for the ECG to be considered normal. The period is the duration of the individual ECG waveform, e.g. from one P wave to the next P-P interval, and the number is the total number of ECGs, normal ones in this case. The next five lines represent the bins of the histograms and the intervals they cover. The numbers between the intervals are the total number of ECGs that fell within that interval.

In compression level 13, each ECG is represented by R(t), which is the time interval from the beginning of the ECG to the point when the R wave peak is recorded. For example, an XML description of a single ECG can be represented as follows:

```
<cardiac cycle>
    <ID>EF3D</ID>
    <length>0.88</length>
    <R>0.17</R>
</cardiac cycle>
```

In this example, EF3D is an identifier for an individual ECG. If a continuous sequence of ECGs is stored, the identifier can be omitted. The length term represents the time interval or duration of the ECG, and R represents the time interval from the beginning of the ECG to the peak of the R wave.

In compression level 12, each ECG is represented as P(t), R(t), and T(t), or the times intervals from the beginning of the ECG to the peaks of the P, R, and T waves, respectively. For example, an XML description of a single ECG can be represented as follows:

```
<cardiac cycle>
    <ID>EF3D</ID>
    <length>0.88</length>
    <P>0.04</P>
    <R>0.17</R>
    <T>0.35</T>
</cardiac cycle>
```

As described above, EF3D is an identifier for an individual ECG. If a continuous sequence of ECGs is stored, the identifier can be omitted. The length term represents the time interval or duration of the ECG, and the values of P, R, and T represent the time intervals from the beginning of the ECG to the peaks of each of the P, R, and T waves.

In compression level 11, each ECG is represented by a QRS interval which is the time interval from the beginning of the ECG to the points representing the start (Q), the peak (R), and the end (S) intervals of the R wave. For example, an XML description of a single ECG can be represented as follows:

```
<cardiac cycle>
    <ID>EF3D</ID>
    <length>0.88</length>
    <R>
        <start>0.14</start>
        <peak>0.17</peak>
        <end>0.19</end>
    </R>
</cardiac cycle>
```

As described above, EF3D is an identifier for an individual ECG and can be omitted if a continuous sequence of ECGs is stored. The length term represents the time interval or duration of the ECG, and the values of start, peak, and end represent the time intervals from the beginning of the ECG to the start, peak, and the end of the R wave intervals.

It should be noted that compression level 11 can provide additional diagnostic information over compression level 12. For example, the width of the QRS complex can be used to identify ventricular anomalies ranging from ventricular hypertrophy to Purkinje damage.

In compression level 10, each ECG is represented by a P, QRS, T and U (if present) interval, which is the time interval from the beginning of the ECG to the points representing the start, the peak, and the end intervals of each of the P, R, T, and U waves. For example, an XML description of a single ECG can be represented as follows:

```
<cardiac cycle>
    <ID>EF3D</ID>
    <length>0.88</length>
    <P>
        <start>0.00</start>
        <peak>0.04</peak>
        <end>0.08</end>
    </P>
    <R>
        <start>0.14</start>
        <peak>0.17</peak>
        <end>0.19</end>
    </R>
    <T>
        <start>0.29</start>
        <peak>0.35</peak>
        <end>0.38</end>
    </T>
    <U> (if present)
        <start>0.45</start>
        <peak>0.52</peak>
        <end>0.58</end>
    </U>
</cardiac cycle>
```

As described above, EF3D is an identifier for an individual ECG and can be omitted if a continuous sequence of ECGs is stored. The length represents the time interval or duration of the ECG, and the values of start, peak, and end represent the time intervals from the beginning of the ECG to the start, peak, and the end of each of the P, R, T, and U wave intervals.

In compression level 9, each segment of the ECG can be tokenized by a Bezier curve. The application of a Bezier curve to the ECG is well within the ability of one skilled in the art. In one example, an XML description of segments of an ECG can be represented as follows:

```
<Token ID="name000345">
    <Bezier section name="P wave">
        <!-Bezier curve details here-!>
        <start>0.00</start>
        <end>0.082</end>
    </Bezier section>
    <Bezier section name="TP interval">
        <!-Bezier curve details here-!>
        <start>0.355</start>
        <end>0.911</end>
    </Bezier section>
</Token>
```

In this form of compression, specific segments of the ECG can be represented by a Bezier curve token. The "Bezier curve details here" line would contain the details of the polynomial equation that defines the curve. The Token ID field would represent a unique identifier for a particular token. Also, the residual information between the token and the actual ECG would be discarded.

In compression level 8, the ECG can be represented by a template ECG. In this case the ECG could be matched with the closest approximation from a group of templates. The best template is selected and the residual information between the template and the ECG is discarded. The template can include the previous ECG, the autoregressive moving average ECG, specific digitally "synthetic" ECG, "population representative" ECG, or any other template known to one skilled in the art. For example, an XML description of a particular template can be utilized as follows:

```
<Template>
    <ID="3gT8& @ @ dfs"/>
    <type="DATABASE"/>
    <location=URL address>
<Template/>
```

A specific template is identified in the ID field, it is located in a database, and the location of the database is represented by a URL address. The database can be remote from the signal recorder, or it may be present within the device in, for example, RAM or ROM memory.

In compression level 7, the ECG can be tokenized by utilizing a Bezier curve approximation as in compression level 9. In this case, however, the residual information between the ECG and the Bezier curve token is preserved. This residual can be further tokenized as in compression level 9 or templated as in compression level 8.

In compression level 6, the ECG can be templated as in compression level 8. In this case, however, the residual information between the ECG and the template is preserved. This residual can be further tokenized as in compression level 9 or templated as in compression level 8.

In compression level 5, the ECG can be tokenized by utilizing a Bezier curve approximation as in compression level 9. The residual information between the ECG and the Bezier curve token is preserved. This residual can be further compressed by utilizing a lossy compression method such as, but not limited to, wavelet, fractal, transform, vector quantization encoding, and combinations thereof.

In compression level 4, the ECG can be templated as in compression level 8. The residual information between the ECG and the template is preserved. This residual can be further compressed by utilizing a lossy compression method such as, but not limited to, wavelet, fractal, transform, vector quantization encoding, and combinations thereof.

In compression level 3, the ECG can be tokenized by utilizing a Bezier curve approximation as in compression level 9. The residual information between the ECG and the Bezier curve token is preserved. This residual can be further compressed by utilizing a lossless compression method such as, but not limited to, run-length, statistical (pattern substitution, Huffman), differential and differential Huffman, predictive encoding, and combinations thereof. For example, an XML description of such compression can be represented as follows:

```
<CompressionScheme>
    <Token ID="name000345">
        <Bezier section name="P wave">
            <!-Bezier curve details here-!>
            <start>0.00</start>
            <end>0.082</end>
        </Bezier section>
        <!-other sections that are part of the ECG
        waveform are not listed here->
        <Bezier section name="TP interval">
```

-continued

```
        <!-Bezier curve details here-!>
            <start>0.355</start>
            <end>0.911</end>
        </Bezier section>
    </Token>
    <ResidualCompressionScheme>
        <Type>RunLengthEncoding<Type/>
        <Algorithm>RLEmethod12<Algorithm/>
    <ResidualCompressionScheme/>
<CompressionScheme/>
```

In this compression scheme, the P wave and the TP interval are tokenized with a Bezier curve. The residual is then compressed with a run length encoding algorithm.

In compression level 2, the ECG can be templated as in compression level 8. The residual information between the ECG and the template is preserved. This residual can be further compressed by utilizing a lossless compression method such as, but not limited to, run-length, statistical (pattern substitution, Huffman), differential and differential Huffman, predictive encoding, and combinations thereof. For example, an XML description of such compression can be represented as follows:

```
<CompressionScheme>
    <Template>
        <ID="3gT8& @ @ dfs"/>
        <type="DATABASE"/>
        <location=URL address>
    <Template/>
    <ResidualCompressionScheme>
        <Type>RunLengthEncoding<Type/>
        <Algorithm>RLEmethod12<Algorithm/>
    <ResidualCompressionScheme/>
<CompressionScheme/>
```

In this compression scheme, the ECG is teniplated and the residual is compressed with a run length encoding algorithm.

Compression level 1 can represent any of a multiplicity of schemes in which there is a greater compression for "normal" ECGs and a less compression for "abnormal" ECGs. Similarly, schema for preserving only the most "typical" ECGs or series of ECGs representing different tokens and/or templates can also be contemplated.

In a situation where abnormal ECGs are important for proper medical diagnosis and treatment, one approach to compression with memory storage limitations would be as follows:

1. Save all ECGs as level 9 compression or lower.
2. Save all abnormal ECG's as level 5 compression or lower.
3. Specify nature of "abnormal" ECG.
4. Specify compression algorithm for compression levels 5 and above. In this way, a medical practitioner can specify which aspects of the ongoing ECG recordings are most important to medical diagnosis and treatment, and those aspects can be preserved with the least amount of compression permitted by the memory storage limitations. The less preferred normal ECGs in this case are preserved at least at compression level 9. At this compression level, however, it is still possible to overrun the memory storage. Thus, the specified quality (at least level 9) of the signal is maintained, but only the more recent normal ECGs are preserved when the earliest stored normal ECGs have degraded as far as they are allowed (at least level 9) given the amount of available memory storage. In other words, normal ECGs are initially saved at a low compression level, and are gradually compressed over time to compression level 9. At this point, further collection of the physiological signal causes these earlier collected normal ECGs to be dumped from memory storage. The same situation applies to the abnormal ECGs, which are initially saved at a low compression level and are dumped from memory storage when they reach compression level 5.

Figure 4:
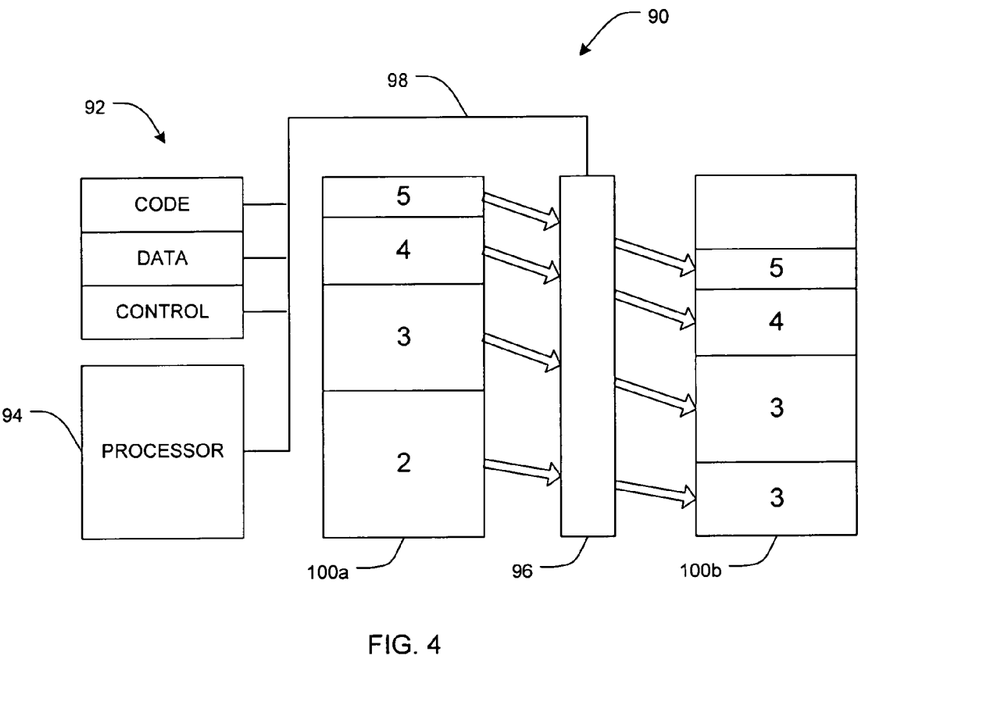
FIG. 4 is a graphical representation of a compression scheme for optimizing retention of signal information from a physiologically generated digital signal in accordance with an embodiment of the present invention.

A graphical representation of such a system 90 can be seen in FIG. 4. Memory storage 92 can contain the stored signal data as well as code for the control, compression, etc, functions of the signal recorder. Also shown is a processor 94, which is connected to a cache 96 by a BUS 98. Graphical representations of the contents of the cache at time $t_1$ 100a, and at a later time $t_2$ 100b are shown. The numbers listed in $t_1$ and $t_2$ represent data in the cache with a given level of compression. For example, 2 is less compressed than 3, 4 is less compressed than 5, etc. At time $t_1$, the cache is essentially full and compression takes place. The data represented by the number 2 is the most recently collected data and thus has the least compression. This data (2) is compressed to a greater level of compression (3) to free up memory storage as shown at $t_2$. This process is continued until all the stored data has reached the maximum allowable compression.

The user can choose how to dispose of old ECGs based on what preferred signal information would be most beneficial to the medical treatment. For example, the abnormal ECGs can be preserved at the expense of normal ECGS. Similarly, the normal ECGs can be preserved at the expense of the abnormal ECGs. Or only the most recent ECGs can be preserved, regardless of their normal/abnormal classification. The user may also specify a prioritized list of abnormal ECGs to be preserved in a specific order.

Alternatively, the user can specify that consecutive ECGs be preserved. It may be more important to preserve runs of 5, 10, or other numbers of consecutive ECGs for later diagnosis. In practice, logging of consecutive ECG abnormalities are of value for diagnosis, both in verifying the presence of a sustained abnormal condition by its reoccurrence as well as providing a measure of the severity of the condition by its sustained presence. Examples of abnormal ECGs requiring multiple consecutive cardiac cycles for reliable diagnosis include ventricular escape as well as atrial abnormalities such as atrial fibrillation and atrial flutter.

Similar compression schemes can also be utilized for other types of physiological signals, such as vectorcardiograms (VCGs). VCGs can be compressed as demonstrated above with ECG data. Some alteration may be required to account for the importance of loop structure and angle in the VCG date. For example, VCGs can be represented by histograms of VCG angles and peak magnitudes of the P, R, and T loops. Similarly, VCG loops can be represented by Bezier curves and templates, with the residual being discarded or compressed as discussed above.

It can also be useful to preserve the correspondence between VCG and ECG events, regardless of the compression technique employed. This correlation can be accomplished by any means known to one skilled in the art, such as: 1) time coding the VCG data to correspond to the ECG data; 2) embedding the VCG data in the same time-stamped packet as the corresponding ECG data; and 3) correlating the VCG by a pointer or unique numeric token identifier associated with the corresponding ECG data.

It is to be understood that the above-referenced arrangements are illustrative of the application for the principles of the present invention. Numerous modifications and alternative arrangements can be devised without departing from the spirit and scope of the present invention while the present invention has been shown in the drawings and described above in connection with the exemplary embodiments(s) of the invention. It will be apparent to those of ordinary skill in the art that numerous modifications can be made without departing from the principles and concepts of the invention as set forth in the claims.

What is claimed is:

1. A method of optimizing retention of signal information from a physiologically generated digital signal, comprising steps of:
    generating a digital signal from a physiological source, the digital signal having an acquisition compression level;
    storing the digital signal into a memory location as a stored digital signal, wherein the stored digital signal has a stored compression level;
    identifying within the stored digital signal a preferred digital signal event exclusive of a non-preferred digital signal event, wherein the preferred digital signal event has higher clinical value than the non-preferred digital signal event;
    detecting a memory storage limitation in the memory location; and
    increasing the stored compression level of at least a portion of the stored digital signal in the memory location as a result of the memory storage limitation in the memory location.

2. A method as in claim 1, wherein the acquisition compression level is no compression.

3. A method as in claim 1, wherein the acquisition compression level is at least some compression.

4. A method as in claim 1, wherein the stored compression level is no compression.

5. A method as in claim 1, wherein the stored compression level is at least some compression.

6. A method as in claim 1, wherein the step of increasing the stored compression level results in a uniform compression of essentially all of the stored digital signal.

7. A method as in claim 1, wherein the preferred digital signal event has a first event compression level and the non-preferred digital signal event has a second event compression level.

8. A method as in claim 7, wherein the first event compression level is different from the second event compression level.

9. A method as in claim 8, wherein the first event compression level is of a lower compression than the second event compression level.

10. A method as in claim 7, further comprising the step of increasing the second event compression level of the non-preferred digital signal event as a result of detecting a memory storage limitation.

11. A method as in claim 7 further comprising steps of:
    determining that the second event compression level of the non-preferred digital signal event cannot be increased; and
    increasing the first event compression level of the preferred digital signal event.

12. A method as in claim 1, further comprising the step of increasing the acquisition compression level of the digital signal in response to detecting a memory storage limitation in the memory location.

13. A method as in claim 1, further comprising step of detecting an energy supply limitation.

14. A method as in claim 13, further comprising decreasing the acquisition compression level of the digital signal.

15. A method as in claim 13, further comprising decreasing the stored compression level of the stored digital signal.

16. A method as in claim 1, further comprising steps of:
    detecting an upload source; and
    uploading the digital signal to the upload source.

17. A method of optimizing retention of signal information from a physiologically generated digital signal, comprising steps of:
    generating a digital signal from a physiological source, the digital signal having an acquisition compression level;
    storing the digital signal into a memory location as a stored digital signal;
    identifying within the stored digital signal a preferred digital signal event exclusive of a non-preferred digital signal event, the preferred digital signal event having a first event compression level and the non-preferred digital signal event having a second event compression level, wherein the preferred digital signal event has higher clinical value than the non-preferred digital signal event;
    detecting a memory storage limitation in the memory location; and
    increasing the second event compression level of the non-preferred digital signal event as a result of detecting a memory storage limitation.

18. A method as in claim 17, wherein the acquisition compression level is no compression.

19. A method as in claim 17, wherein the acquisition compression level is at least some compression.

20. A method as in claim 17, wherein the first event compression level is no compression.

21. A method as in claim 17, wherein the first event compression level is at least some compression.

22. A method as in claim 17, wherein the second event compression level is no compression.

23. A method as in claim 17, wherein the second event compression level is at least some compression.

24. A method as in claim 17, wherein the first event compression level is different from the second event compression level.

25. A method as in claim 17, wherein the first event compression level is of a lower compression than the second event compression level.

26. A method as in claim 17 further comprising steps of:
    determining that the second event compression level of the non-preferred digital signal event cannot be increased; and
    increasing the first event compression level of the preferred digital signal event.

27. A method as in claim 17, further comprising the step of increasing the acquisition compression level of the digital signal in response to detecting a memory storage limitation in the memory location.

28. A method as in claim 17, further comprising a step of detecting an energy supply limitation.

29. A method as in claim 28, further comprising decreasing the acquisition compression level of the digital signal.

30. A method as in claim 28, further comprising decreasing at least one of the first or second event compression levels of the stored digital signal.

31. A method as in claim 17, further comprising steps of:
detecting an upload source; and
uploading the digital signal to the upload source.

32. A system for optimizing retention of signal information from a physiologically generated digital signal, comprising:
- a signal recorder having an online mode and a remote mode;
- an online memory module operationally coupled to the signal recorder when in the online mode, such that the digital signal is stored in the online memory module when the signal recorder is in the online mode;
- a local memory module operationally coupled to the signal recorder when in the remote mode, such that the digital signal is stored in the local memory module as a stored digital signal when the signal recorder is in the remote mode, the stored digital signal being identified as having a preferred digital signal event exclusive of a non-preferred digital signal event, wherein the preferred digital signal event has higher clinical value than the non-preferred digital signal event;
- a local memory monitor operationally coupled to the local memory module to detect a memory storage limitation in the local memory module;
- a compression unit operationally coupled to the local memory module to compress at least a portion of the stored digital signal recorded by the signal recorder, wherein the preferred digital signal event has a first event compression level and the non-preferred digital signal event has a second event compression level;
- a control unit operationally coupled to the local memory module to evaluate a compression level of the stored digital signal; and
- an online detection unit operationally coupled to the control unit to detect when the signal recorder is in the online mode.

33. A system as in claim 32, further comprising an acquisition compression unit operationally coupled to the local memory module to compress the digital signal prior to the digital signal being stored as a stored digital signal in the local memory module.

* * * * *